(12) United States Patent  
Lee et al.

(10) Patent No.: US 9,034,279 B2
(45) Date of Patent: May 19, 2015

(54) BIO-CHIP

(71) Applicant: SAMSUNG ELECTRO-MECHANICS CO., LTD., Suwon, Gyunggi-do (KR)

(72) Inventors: Dong Woo Lee, Gyunggi-do (KR); Bo Sung Ku, Gyunggi-do (KR)

(73) Assignee: Samsung Electro-Mechanics Co., Ltd., Suwon, Gyunggi-do (KR)

( * ) Notice: Subject to any disclaimer, the term of this patent is extended or adjusted under 35 U.S.C. 154(b) by 14 days.

(21) Appl. No.: 13/771,016

(22) Filed: Feb. 19, 2013

(65) Prior Publication Data

US 2014/0162908 A1    Jun. 12, 2014

(30) Foreign Application Priority Data

Dec. 6, 2012    (KR) .................. 10-2012-0140921

(51) Int. Cl.
*B01L 3/00*    (2006.01)
*G01N 33/543*  (2006.01)

(52) U.S. Cl.
CPC ...... *G01N 33/54366* (2013.01); *B01L 3/50853* (2013.01); *B01L 3/5088* (2013.01); *B01L 2200/025* (2013.01); *B01L 2200/028* (2013.01)

(58) Field of Classification Search
CPC ... B01L 3/508; B01L 3/5088; B01L 3/50855; B01L 2300/0819
USPC ................ 422/547, 551, 552, 553, 560, 563
See application file for complete search history.

(56) References Cited

U.S. PATENT DOCUMENTS

| | | | |
|---|---|---|---|
| 6,265,229 B1 | 7/2001 | Fodstad et al. | |
| 2004/0125266 A1 | 7/2004 | Miyauchi et al. | |
| 2004/0185483 A1* | 9/2004 | Stuelpnagel et al. | 435/6 |
| 2011/0027914 A1* | 2/2011 | Bunce et al. | 436/518 |
| 2012/0165224 A1 | 6/2012 | Song et al. | |

FOREIGN PATENT DOCUMENTS

| | | |
|---|---|---|
| JP | 4071824 B2 | 4/2008 |
| JP | 4897192 B2 | 3/2012 |
| KR | 10-2012-0071216 A | 7/2012 |

OTHER PUBLICATIONS

Korean Office Action, w/ English translation thereof, issued in Korean Patent Application No. KR 10-2012-0140921 dated Nov. 27, 2013.

* cited by examiner

*Primary Examiner* — Jill Warden
*Assistant Examiner* — Dwayne K Handy
(74) *Attorney, Agent, or Firm* — McDermott Will & Emery LLP

(57) ABSTRACT

There is provided a bio-chip, including a fixing plate having a plurality of guide grooves formed in one surface thereof, a first substrate having a plurality of support plates inserted into the guide grooves, and a plurality of pillars protruded from one surface of the respective support plates, and having a biomaterial disposed thereon.

13 Claims, 5 Drawing Sheets

BIO-CHIP

CROSS-REFERENCE TO RELATED APPLICATIONS

This application claims the priority of Korean Patent Application No. 10-2012-0140921 filed on Dec. 6, 2012, in the Korean Intellectual Property Office, the disclosure of which is incorporated herein by reference.

BACKGROUND OF THE INVENTION

1. Field of the Invention

The present invention relates to a bio-chip, and more particularly, to a bio-chip allowing for individual experiments to be performed on biomaterials attached thereto.

2. Description of the Related Art

Recently, research and development of biotechnological means for rapidly diagnosing various human diseases have been increasingly demanded. For this reason, bio-chips or cell chips necessary for testing biomaterials have constantly been developed.

Bio-chips or cell chips are useful in testing large amounts of biomaterials, and thus may be used by pharmaceutical and cosmetics companies as well as in hospitals.

Bio-chips may be classified into DNA chips, protein chips, and cell chips, depending on the kind of a biomaterial fixed to a substrate. Previously, DNA chips were largely evident, in concert with understanding human genetic information. However, with increasing interest in the proteins that underlie all life, and cells that are the backbone of life as binders for proteins, protein chips and cell chips have recently come to prominence.

Meanwhile, in the pharmaceutical industry, the cosmetics industry, and others, a method of verifying the effectiveness and stability (toxicity) of a specific drug by testing reactions of cells to the specific drug has been used. However, since the existing methods require large amounts of reagents for precise tests, such methods may be relatively expensive and consume a lot of time.

Accordingly, there is a need for the development of a bio-chip allowing for fast and accurate diagnoses, as well as reductions in costs associated therewith.

According to the related art, when the biomaterials attached to the bio-chip are analyzed, the entire bio-chip needs to be used, even in a case in which only some biomaterials are to be analyzed.

Therefore, the research into bio-chips capable of separating and analyzing only portions of the biomaterials attached thereto is needed.

SUMMARY OF THE INVENTION

An aspect of the present invention provides a bio-chip capable of separating and analyzing only biomaterials corresponding to selected regions in all the biomaterials attached to a single bio-chip.

According to an aspect of the present invention, there is provided a bio-chip, including: a fixing plate having a plurality of guide grooves formed in one surface thereof; a first substrate having a plurality of support plates inserted into the guide grooves; and a plurality of pillars protruded from one surface of the respective support plates, and having a biomaterial disposed thereon.

The plurality of support plates may be connected to one another by connecting members.

The guide groove may be formed in a length direction.

Here, the guide groove may include a magnetic substance provided therein.

Here, the support plate may have a magnetic material coated on an upper surface thereof.

The support plate may be formed of metal.

Here, the guide groove may be provided with a chamfer portion formed at an edge of a side wall thereof.

The bio-chip may further include a second substrate having a plurality of micro-wells into which the pillars are inserted.

According to another aspect of the present invention, there is provided a bio-chip, including: a fixing plate; and a first substrate having a plurality of support plates, and a plurality of pillars protruded from one surface of the respective support plates so as to dispose a biomaterial thereon, wherein the first substrate is insertion-combined with an side surface of the fixing plate in a length direction.

The fixing plate may have a plurality of guide holes passing through both side surfaces thereof, the support plates being insertion-combined with the guide holes.

Here, a width of the guide hole may increase toward an upper end thereof in a height direction.

The plurality of support plates may be connected to one another by connecting members.

The support plate may have a first side surface and a second side surface, and a protrusion portion protruded from the first side surface so as to facilitate attachment or detachment of the first substrate.

Here, a side wall of the guide hole may have a sloped surface.

Here, an upper surface and a lower surface of the first substrate may have different areas.

Here, the guide hole may be provided with a catching member formed on one side thereof so as to restrict movement of the first substrate.

BRIEF DESCRIPTION OF THE DRAWINGS

The above and other aspects, features and other advantages of the present invention will be more clearly understood from the following detailed description taken in conjunction with the accompanying drawings, in which.

DETAILED DESCRIPTION OF THE EMBODIMENTS

Hereinafter, embodiments of the present invention will be described in detail with reference to the accompanying drawings. The invention may, however, be embodied in many different forms and should not be construed as being limited to the embodiments set forth herein.

Rather, these embodiments are provided so that this disclosure will be thorough and complete, and will fully convey the scope of the invention to those skilled in the art.

Figure 1:
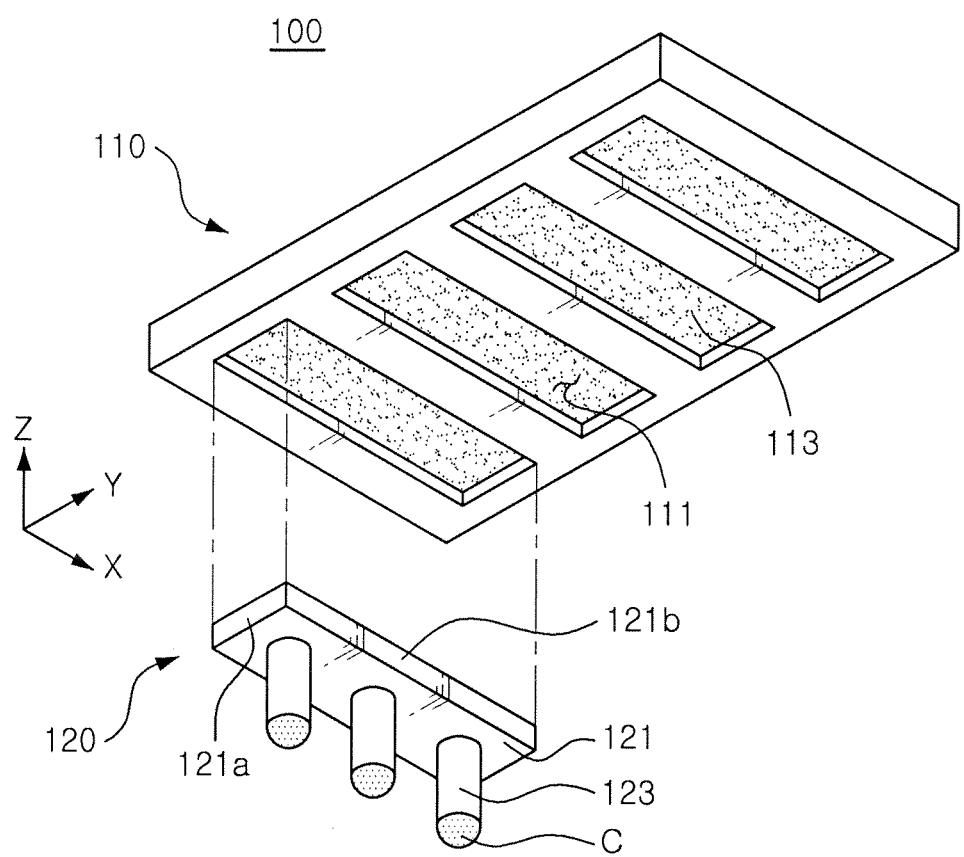
FIG. 1 is an exploded perspective view of a fixing plate and a first substrate according to an embodiment of the present invention.
Figure 2:
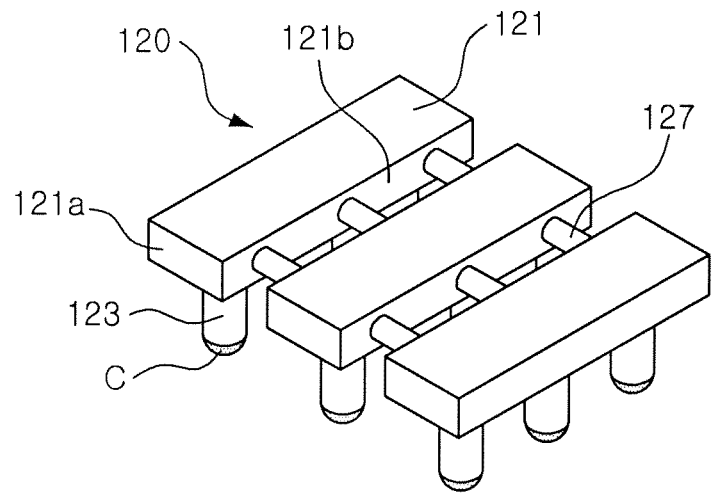
FIG. 2 is a perspective view of the first substrate according to the embodiment of the present invention.

FIG. 1 is an exploded perspective view of a fixing plate and a first substrate according to an embodiment of the present invention; and FIG. 2 is a perspective view of the first substrate according to the embodiment of the present invention.

Figure 3:
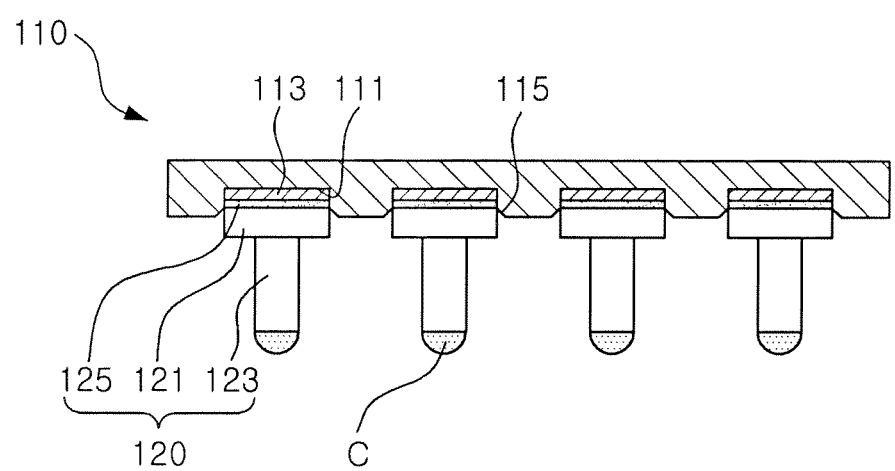
FIG. 3 is a cross-sectional view of a combination of the fixing plate and the first substrate according to the embodiment of the present invention.
Figure 4:
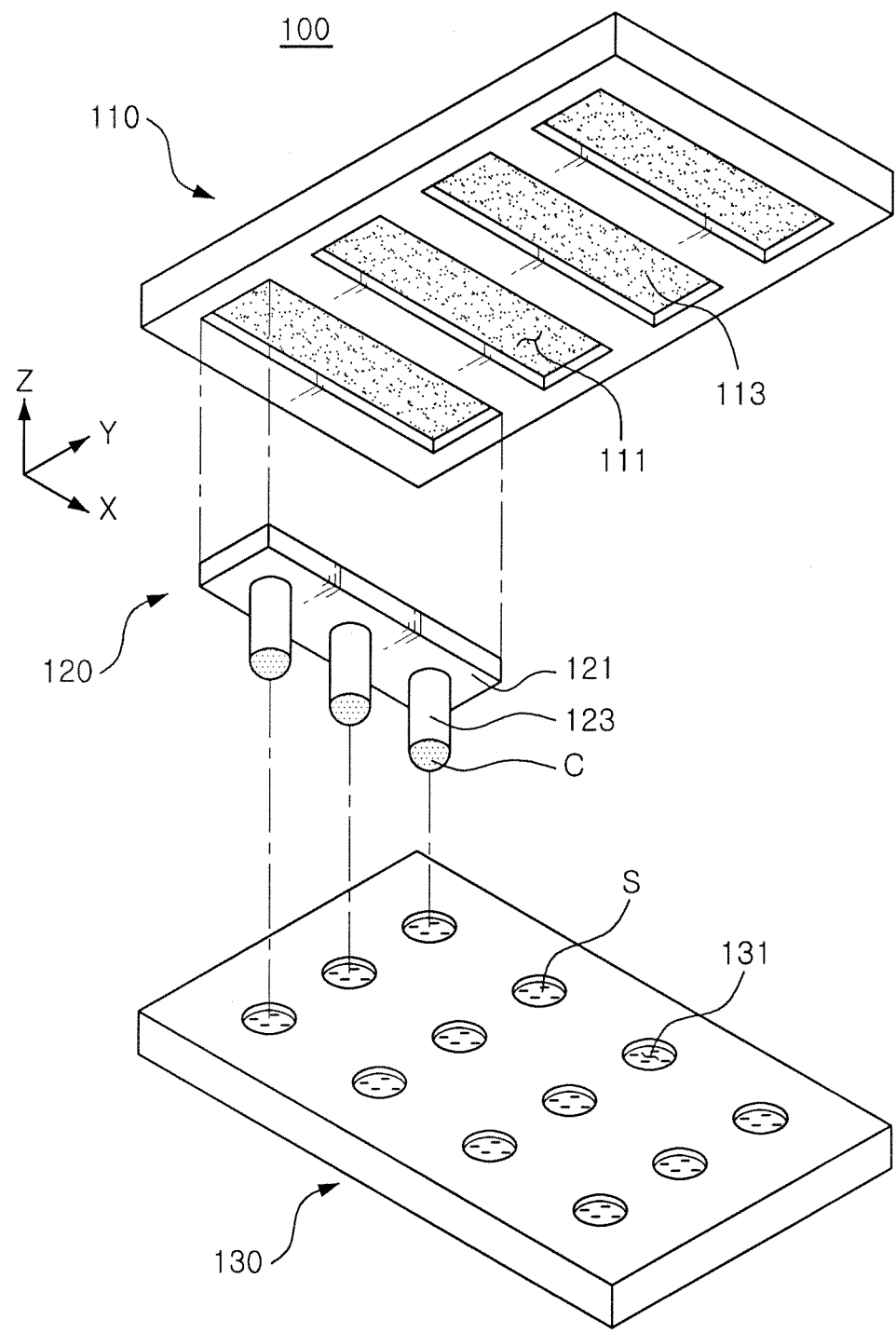
FIG. 4 is an exploded perspective view of a bio-chip according to the embodiment of the present invention.

In addition, FIG. 3 is a cross-sectional view of a combination of the fixing plate and the first substrate according to the embodiment of the present invention; and FIG. 4 is an exploded perspective view of a bio-chip according to the embodiment of the present invention.

Referring to FIGS. 1 through 4, a bio-chip 100 according to an embodiment of the present invention may include a fixing plate 110, a first substrate 120, and a second substrate 130.

The fixing plate 110 may generally have a thin plate shape as shown in FIG. 1.

Specifically, the fixing plate 110 may have a rectangular shape having a predetermined length and width, and may be formed of plastic.

A plurality of guide grooves 111 may be provided in one surface of the fixing plate 110. The guide grooves 111 may be formed with a predetermined interval therebetween in the fixing plate 110 while having a predetermined depth.

In addition, the guide groove 111 may be formed by depressing a portion of a lower surface of the fixing plate 110, and may be formed in a length direction (Y-axis direction) of the fixing plate 110.

A biomaterial C may be disposed in the first substrate 120, and to this end, the first substrate 120 may have a plurality of pillars 123.

In detail, the first substrate 120 may have a plurality of pillars 123 extended in a height direction (Z-axis direction), and the plurality of pillars 123 may be protruded from one surface of a support plate 121, to be described below.

All of the plurality of pillars 123 may have the same length, and may be arranged with a predetermined interval therebetween along the X-axis and Y-axis.

A cross section of the pillar 123 may be circular, quadrangular, or polygonal.

Also, an end portion of the pillar 123 may be roughly processed so as to allow the biomaterial C to be easily attached thereon. Alternatively, an auxiliary material helping attachment of the biomaterial C may be further coated on the end portion of the pillar 123.

Here, the first substrate 120 may be inserted into the guide grooves 111, to thereby be combined with the fixing plate 110.

Specifically, the first substrate 120 may include a plurality of support plates 121, and the plurality of support plates 121 are inserted into the guide grooves 111 so that the first substrate 120 may be combined with the fixing plate 110.

The first substrate 120 may have a structure in which the plurality of support plates 121 are connected to one another by connecting members 127. The support plate 121 may have first side surfaces 121a facing each other in the X-axis direction and second side surfaces 121b facing each other in the Y-axis direction.

That is, the connecting members 127 are attached to the second side surfaces 121b of the plurality of support plates 121 to connect the plurality of support plates 121 to one another.

The first substrate 120 may be separated into the plurality of support plates 121 by removing the connecting members 127. The support plates 121 may be inserted into the guide grooves 111 in a state in which they are separated from one another, or the support plates 121 may be inserted into the guide grooves 111 while they are connected to one another by the connecting members 127.

Here, a magnetic substance 113 may be attached on the guide grooves 111, and in this case, a magnetic material 125 may be coated on an upper surface of the support plate 121 or the support plate 121 may be formed of metal.

Therefore, magnetic force of the magnetic substance 113 may enhance adhesive strength between the support plate 121 and the fixing plate 110.

In addition, a chamfer portion 115 is provided at the edge of a side wall that forms the guide groove 111, to thereby widen a lower end of the guide groove 111, so that the support plate 121 may be easily inserted into the guide groove 111.

The second substrate 130 may generally have a thin plate shape as shown in FIG. 4.

Specifically, the second substrate 130 may have a rectangular parallelepiped shape having predetermined length and width.

The second substrate 130 may include a plurality of micro-wells 131 receiving a medication or reagent S or the like therein. The micro-wells 131 may be disposed with a predetermined interval therebetween, and the pillar 123 may be inserted into the micro-well 131.

In addition, the micro-wells 131 may be formed to have the number of and an interval therebetween, corresponding to the pillars 123 of the first substrate 120.

The biomaterial C and the medication or reagent S are disposed in the first substrate 120 and the second substrate 130 when they are contacted with each other when the first substrate 120 and the second substrate 130 are combined with each other, and thus a reaction of the biomaterial C to the medication or reagent S may be measured.

The second substrate 130 may be formed of plastic.

Since the second substrate 130 formed of plastic may be mass-produced through molding, the production costs thereof may be lowered as compared to a glass bio-chip.

Also, the second substrate 130 formed of plastic is relatively light and have relatively low brittleness as compared with a glass substrate, and thus may be easily handled, resulting in lowering occurrence of damage due to mishandling.

The first substrate 120 may be separated into the plurality of support plates 121 by removing the connecting members 127 therefrom, and thus, the biomaterial C attached to the respective support plates 121 may be individually analyzed.

In addition, the magnetic substance 113 is provided in the guide groove 111, and thus attachment or detachment of the support plate 121 may be easily conducted by magnetic force of the magnetic substance 113.

Figure 5:
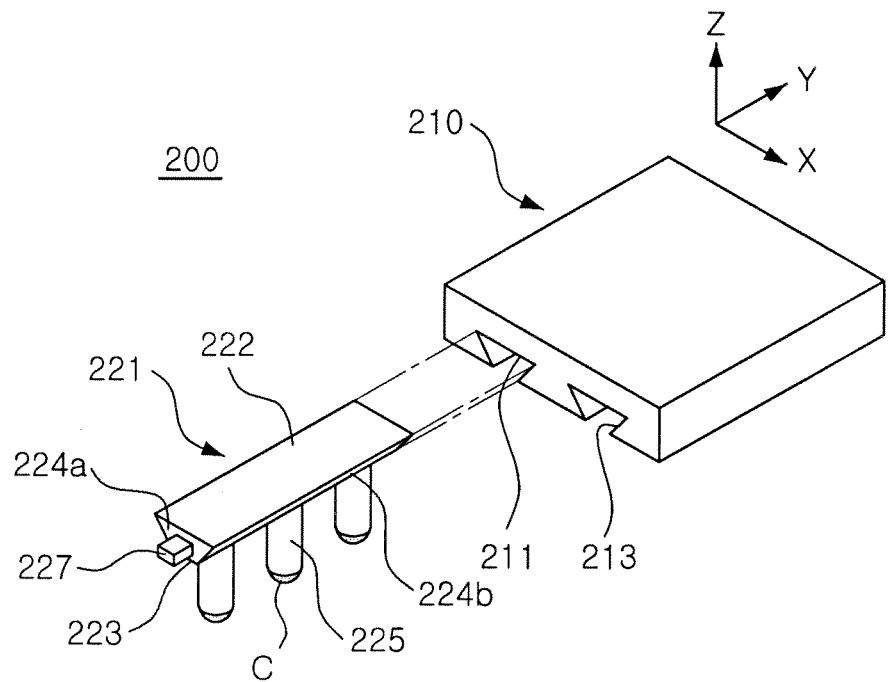
FIG. 5 is a perspective view of a fixing plate and a first substrate according to another embodiment of the present invention.
Figure 6:
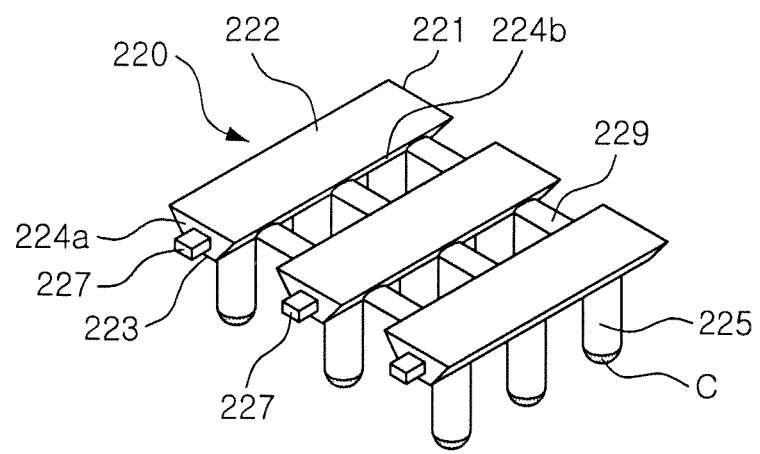
FIG. 6 is a perspective view of the first substrate according to another embodiment of the present invention.

FIG. 5 is a perspective view of a fixing plate and a first substrate according to another embodiment of the present invention; FIG. 6 is a perspective view of the first substrate according to another embodiment of the present invention; and FIG. 7 is a perspective view of bottom surfaces of the fixing plate and the first substrate according to another embodiment of the present invention.

Figure 7:
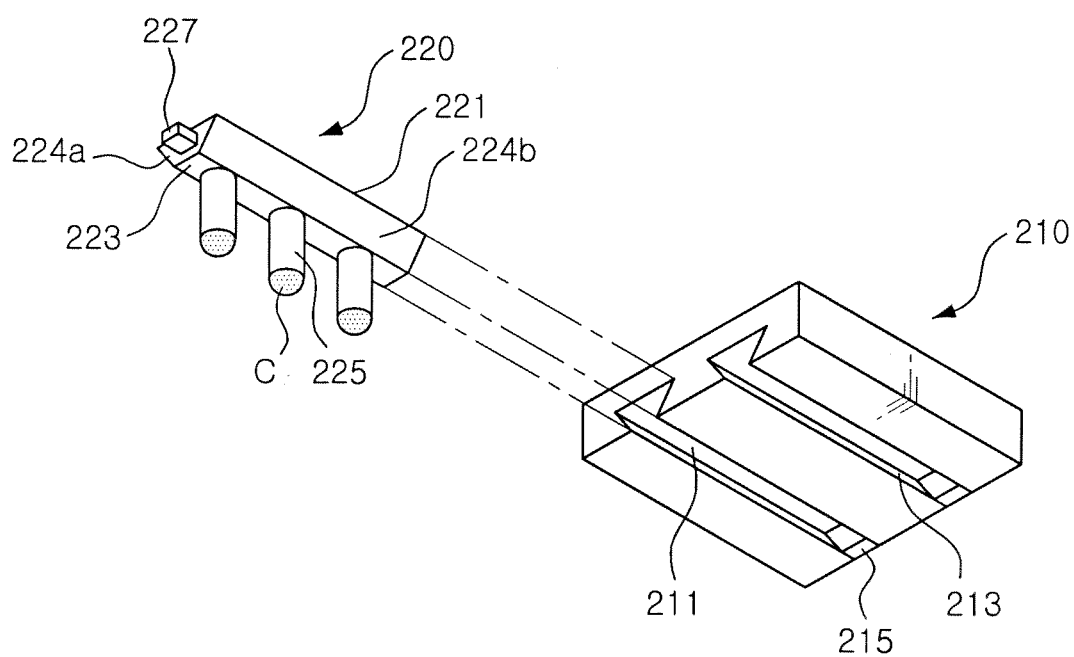
FIG. 7 is a perspective view of bottom surfaces of the fixing plate and the first substrate according to another embodiment of the present invention.

Referring to FIGS. 5 through 7, a bio-chip 200 according to another embodiment of the present invention may include a fixing plate 210 and a first substrate 220.

The fixing plate 210 may generally have a thin plate shape as shown in FIG. 5.

Specifically, the fixing plate 210 may have a rectangular parallelepiped shape having predetermined length and width, and may be formed of plastic.

A plurality of guide holes 211 may be provided in the fixing plate 210, passing through both surfaces of the fixing plate 210. The guide holes 211 may have a predetermined depth and be formed with a predetermined interval therebetween in the fixing plate 210.

In addition, the guide hole 211 may be formed in a length direction (Y-axis direction) of the fixing plate 210.

Here, a side wall forming the guide hole 211 in the fixing plate 210 has a sloped surface 213. As the width of the guide hole 211 increases toward an upper end thereof in a height direction (Z-axis direction).

A biomaterial C may be disposed in the first substrate 220, and to this end, the first substrate 220 may have a plurality of pillars 225.

Specifically, the first substrate 220 may have a plurality of pillars 225 extended in a Z-axis direction.

All of the plurality of pillars 225 may have the same length, and may be arranged with a predetermined interval therebetween along the X-axis and Y-axis.

A cross section of the pillar 225 may be circular, quadrangular, or polygonal.

Also, an end portion of the pillar 225 may be roughly processed so as to allow the biomaterial C to be easily attached thereon. Alternatively, an auxiliary material helping attachment of the biomaterial C may be further coated on the end portion of the pillar 225.

Here, the first substrate 220 may have a plurality of support plates 221, and the first substrate 220 may be insertion-combined with a side surface of the fixing plate 210 in a length direction (Y-axis direction).

Specifically, the support plate 221 is insertion-combined with the guide hole 211, whereby the first substrate 220 may be combined with the fixing plate 210.

The first substrate 220 may have a structure in which the plurality of support plates 221 are connected to one another by connecting members 229. The support plate 221 may have first side surfaces 224a facing each other in the Y-axis direction and second side surfaces 224b facing each other in the X-axis direction.

That is, the connecting members 229 are attached to the second side surfaces 224b of the plurality of support plates 221 to connect the plurality of support plates 221 to one another.

Here, the second side surface 224b may be a sloped surface. That is, the plurality of support plates 221 each may have a shape corresponding to the guide hole 211.

Since the second side surface 224b of the support plate 221 included in the first substrate 220 has the sloped surface, an upper surface 222 and a lower surface 223 of the support plate 221 may have different areas.

That is, the lower surface 223 of the support plate 221 may have a smaller area than the upper surface 222 of the support plate 221.

The reason is that the support plate 221 is prevented from being separated from the guide hole 211 when the support plate 221 is inserted into the guide hole 211.

The first substrate 220 may be inserted into the guide hole 211 in the Y-axis direction.

The first substrate 220 may be separated into the plurality of support plates 221 by removing the connecting members 229 therefrom. The plurality of support plates 221 may be inserted into the guide holes 211 while they are separated from one another, or the plurality of support plates 221 may be inserted into the guide holes 211 while they are connected to one another by the connecting members 229.

Meanwhile, a protrusion portion 227 may be provided on the first side surface 224a of the support plate 221, so as to facilitate attachment or detachment of the first substrate 220.

With respect to attaching and detaching procedures of the support plate 221, first, a predetermined force is applied to the protrusion portion 227 provided on the support plate 221, to thereby push the support plate 221 into the guide hole 211, so that the support plate 221 may be inserted into the guide hole 211.

In addition, the protrusion portion 227 is pulled out, so that the support plate 221 inserted into the guide hole 211 may be easily detached therefrom.

Meanwhile, a catching member 215 may be provided on one side of the guide hole 211 so as to restrict movement of the first substrate 220.

Therefore, in the case in which the first substrate 220 is inserted into the guide hole 211 and moved in a Y-axis direction, the movement of the first substrate 220 in the Y-axis direction may be restricted by the catching member 215 after the first substrate 220 is sufficiently inserted into the guide hole 211, and thus the first substrate 220 and the fixing plate 210 may be stably combined with each other.

Here, the guide hole 211 is formed such that only one of the side surfaces of the fixing plate 210 is opened, and thus, one side surface of the fixing plate 210 may be closed. In this case, the closed side surface of the fixing plate 210 may serve as the catching member 215.

Through the foregoing embodiments, the bio-chip 200 according to the embodiment of the present invention allows an individual analysis of the biomaterial C attached to the respective support plates 221 since the connecting members 229 of the first substrate 220 are removed to thereby enable separation into the plurality of support plates 221.

In addition, the support plate 221 may be stably combined with the fixing plate 210 by changing the shape of the guide hole 211.

In addition, the support plate 221 may be easily attached to or detached from the fixing plate 210 by forming the protrusion portion 227 on the first side surface 224a of the support plate 221.

As set forth above, according to the bio-chip according to an embodiment of the present invention, only the biomaterials corresponding to selected regions in all the biomaterials attached to a single bio-chip may be separated and analyzed.

Therefore, various analysis procedures may be conducted through a single bio-chip.

Further, only the biomaterials corresponding to the selected regions of the bio-chip may be easily attached or detached by a magnetic substance.

While the present invention has been shown and described in connection with the embodiments, it will be apparent to those skilled in the art that modifications and variations can be made without departing from the spirit and scope of the invention as defined by the appended claims.

What is claimed is:
1. A bio-chip, comprising:
a fixing plate having a plurality of guide grooves formed in one surface thereof;
a first substrate having a plurality of support plates inserted into the guide grooves;
a plurality of pillars protruded from one surface of the respective support plates, and having a biomaterial disposed thereon; and
a second substrate having a plurality of micro-wells into which the pillars are inserted, wherein the plurality of support plates are separably connected to one another by connecting members.
2. The bio-chip of claim 1, wherein the guide groove is formed in a length direction.

3. The bio-chip of claim 1, wherein the guide groove includes a magnetic substance provided therein.

4. The bio-chip of claim 3, wherein the support plate has a magnetic material coated on an upper surface thereof.

5. The bio-chip of claim 3, wherein the support plate is formed of metal.

6. The bio-chip of claim 1, wherein the guide groove is provided with a chamfer portion formed at an edge of a side wall thereof.

7. A bio-chip, comprising:
   a fixing plate; and
   a first substrate having a plurality of support plates, and a plurality of pillars protruded from one surface of the respective support plates so as to dispose a biomaterial thereon; and
   a second substrate having a plurality of micro-wells into which the pillars are inserted,
   wherein the first substrate is insertion-combined with a side surface of the fixing plate in a length direction, and the plurality of support plates are separably connected to one another by connecting members.

8. The bio-chip of claim 7, wherein the fixing plate has a plurality of guide holes passing through both side surfaces thereof, the support plates being insertion-combined with the guide holes.

9. The bio-chip of claim 8, wherein a width of the guide hole increases toward an upper end thereof in a height direction.

10. The bio-chip of claim 7, wherein the support plate has a first side surface and a second side surface, and a protrusion portion protruded from the first side surface so as to facilitate attachment or detachment of the first substrate.

11. The bio-chip of claim 8, wherein a side wall of the guide hole has a sloped surface.

12. The bio-chip of claim 7, wherein an upper surface and a lower surface of the first substrate have different areas.

13. The bio-chip of claim 8, wherein the guide hole is provided with a catching member formed on one side thereof so as to restrict movement of the first substrate.

* * * * *